(12) United States Patent
Portney et al.

(10) Patent No.: US 9,622,855 B2
(45) Date of Patent: Apr. 18, 2017

(54) REMOTE MULTIFOCAL TO MONOFOCAL OPTIC CONVERSION

(71) Applicants: Valdemar Portney, Newport Coast, CA (US); Nathaniel G. Portney, San Diego, CA (US)

(72) Inventors: Valdemar Portney, Newport Coast, CA (US); Nathaniel G. Portney, San Diego, CA (US)

( * ) Notice: Subject to any disclaimer, the term of this patent is extended or adjusted under 35 U.S.C. 154(b) by 439 days.

(21) Appl. No.: 14/039,322

(22) Filed: Sep. 27, 2013

(65) Prior Publication Data

US 2014/0100654 A1 Apr. 10, 2014

Related U.S. Application Data

(63) Continuation of application No. PCT/US2013/063469, filed on Oct. 4, 2013.

(60) Provisional application No. 61/711,092, filed on Oct. 8, 2012.

(51) Int. Cl.
*A61F 2/16* (2006.01)

(52) U.S. Cl.
CPC .......... *A61F 2/1618* (2013.01); *A61F 2/1601* (2015.04); *A61F 2/1654* (2013.01)

(58) Field of Classification Search
CPC .............................. A61F 2/1618; A61F 2/1635
USPC ............. 623/6.13, 6.37; 351/159.03, 159.18, 351/159.61
See application file for complete search history.

(56) References Cited

U.S. PATENT DOCUMENTS

| | | | |
|---|---|---|---|
| 4,512,040 A * | 4/1985 | McClure | 623/6.13 |
| 4,816,031 A * | 3/1989 | Pfoff | 417/413.3 |
| 5,225,858 A | 7/1993 | Portney | |
| 6,730,123 B1 * | 5/2004 | Klopotek | 623/6.22 |
| 7,073,906 B1 | 7/2006 | Portney | |
| 7,988,285 B2 | 8/2011 | Sandstedt et al. | |
| 8,231,673 B2 | 7/2012 | Sacharoff et al. | |
| 8,287,593 B2 | 10/2012 | Portney | |
| 8,608,800 B2 * | 12/2013 | Portney | 623/6.37 |
| 9,364,319 B2 * | 6/2016 | Portney | G02C 7/085 |
| 2002/0188351 A1 * | 12/2002 | Laguette | A61F 2/1613 623/6.24 |
| 2003/0149480 A1 * | 8/2003 | Shadduck | 623/6.41 |
| 2004/0169816 A1 * | 9/2004 | Esch | 351/160 R |
| 2004/0190153 A1 * | 9/2004 | Esch | 359/666 |
| 2005/0119740 A1 * | 6/2005 | Esch et al. | 623/6.37 |

(Continued)

*Primary Examiner* — Paul Prebilic
(74) *Attorney, Agent, or Firm* — Hackler Daghighian Martino & Novak

(57) ABSTRACT

An ophthalmic multifocal switchable lens includes a deformable element manifesting elevated strain with a formable surface of a multifocal surface shape to provide far and near vision. A transparent chamber is filled with optical matching fluid adjacent to the side of the deformable element opposite to the formable surface. The optical matching fluid has a refractive index that matches a refractive index of the deformable element material. A holding chamber is also filled with the optical matching fluid and connected with the transparent chamber with a means for preventing the optical fluid from being transported from the holding chamber to the transparent chamber which would reduce a strain of the deformable element. A split of light between far and near vision of the multifocal switchable lent changes upon a removal of the means to allow a flow of the optical matching fluid into the transparent chamber.

17 Claims, 7 Drawing Sheets

(56) References Cited

U.S. PATENT DOCUMENTS

| | | | |
|---|---|---|---|
| 2006/0161252 A1* | 7/2006 | Brady | A61F 2/1613 623/6.37 |
| 2007/0030573 A1* | 2/2007 | Batchko | G02B 26/005 359/665 |
| 2008/0161914 A1* | 7/2008 | Brady | A61F 2/1635 623/6.46 |
| 2010/0179653 A1* | 7/2010 | Argento et al. | 623/6.13 |
| 2012/0140167 A1* | 6/2012 | Blum | A61F 2/1624 351/159.34 |
| 2013/0035760 A1* | 2/2013 | Portney | 623/6.13 |
| 2014/0232982 A1* | 8/2014 | Iwai | 351/159.03 |

* cited by examiner

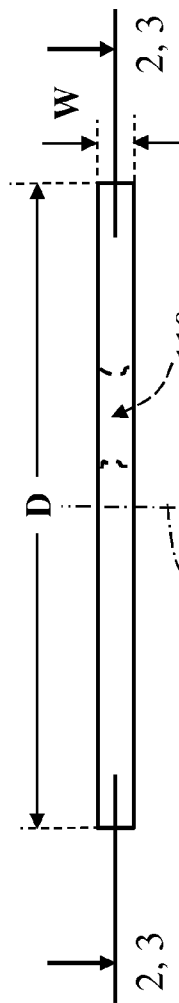
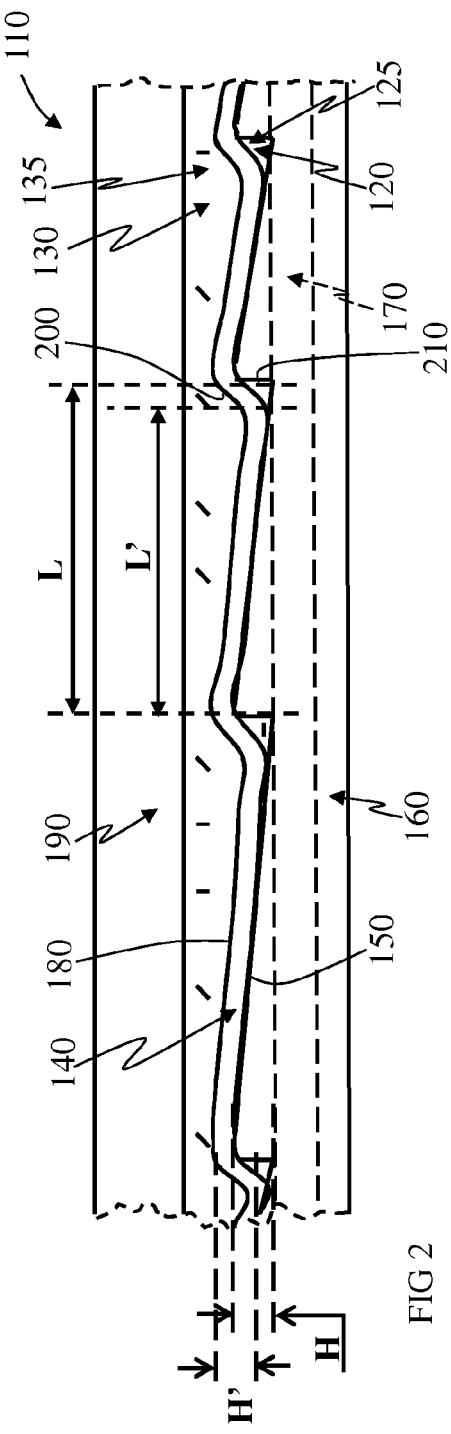
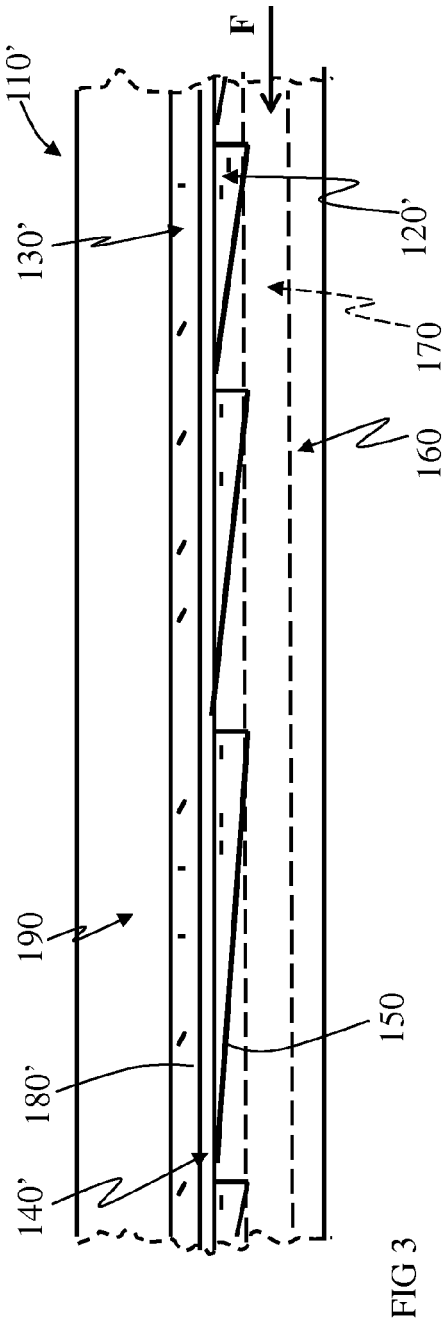

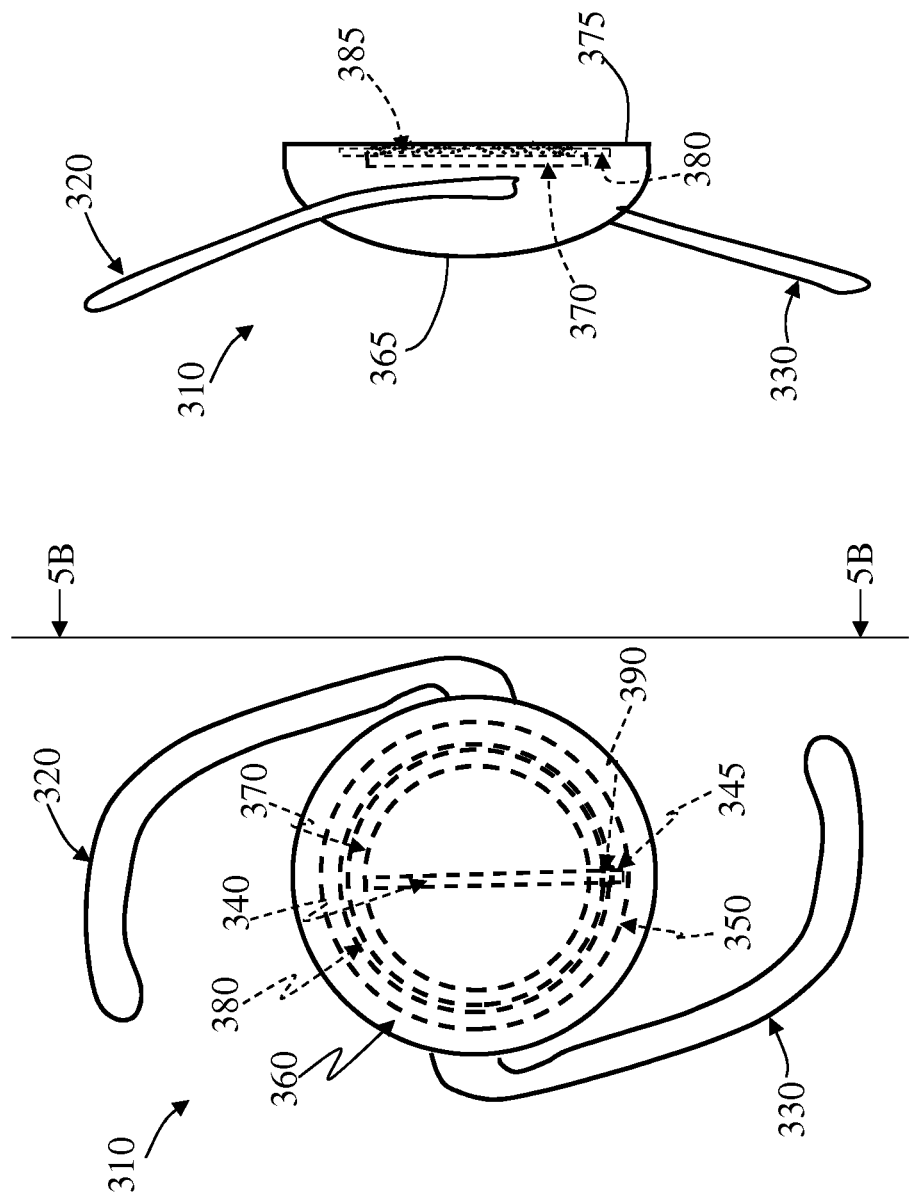

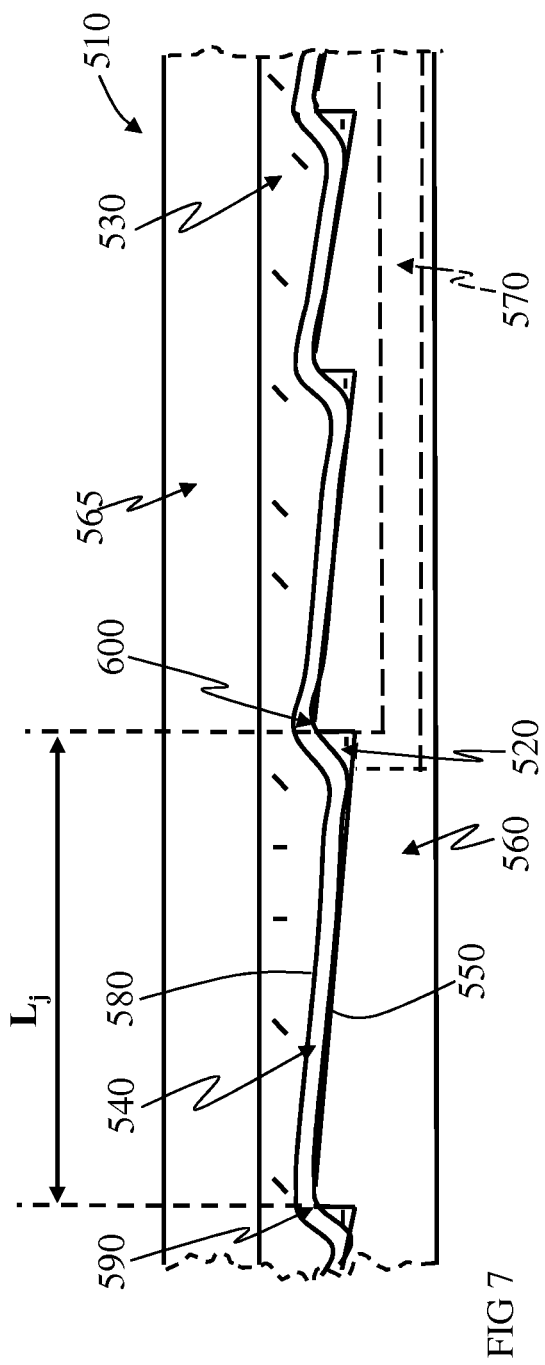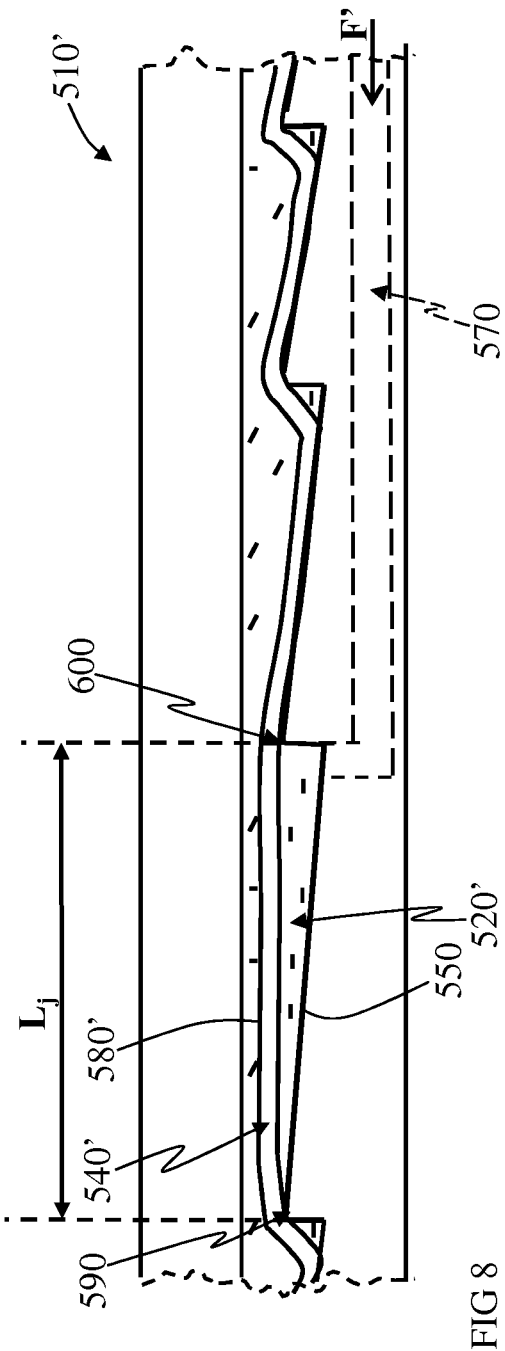

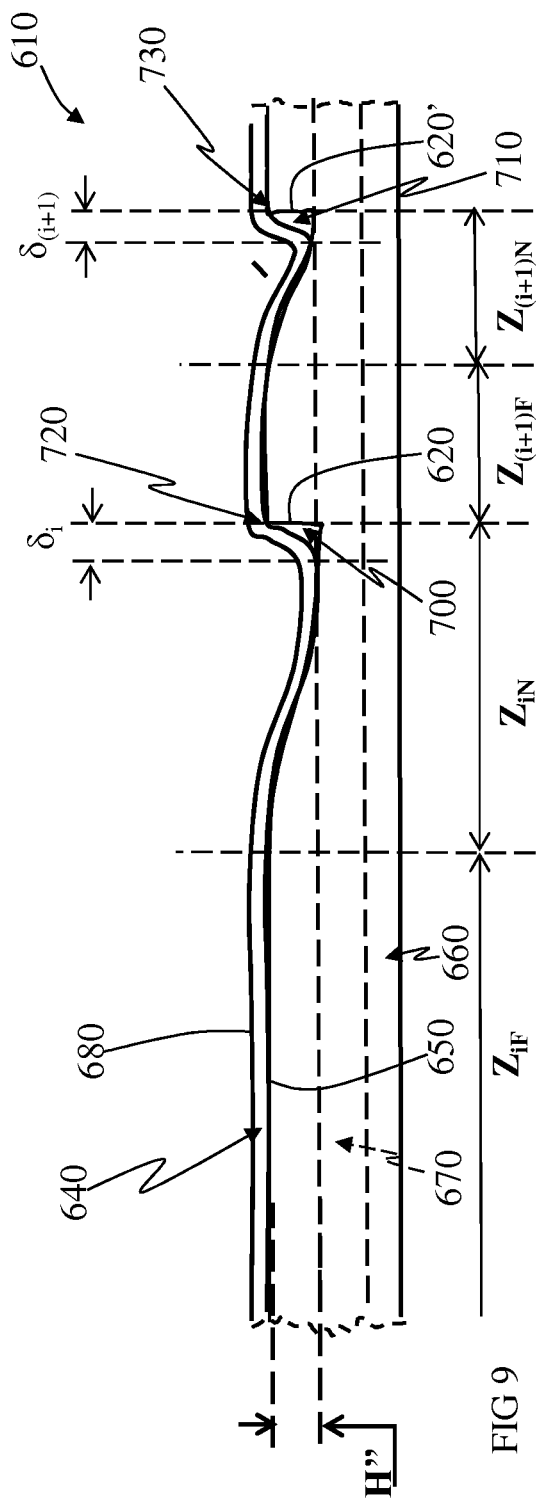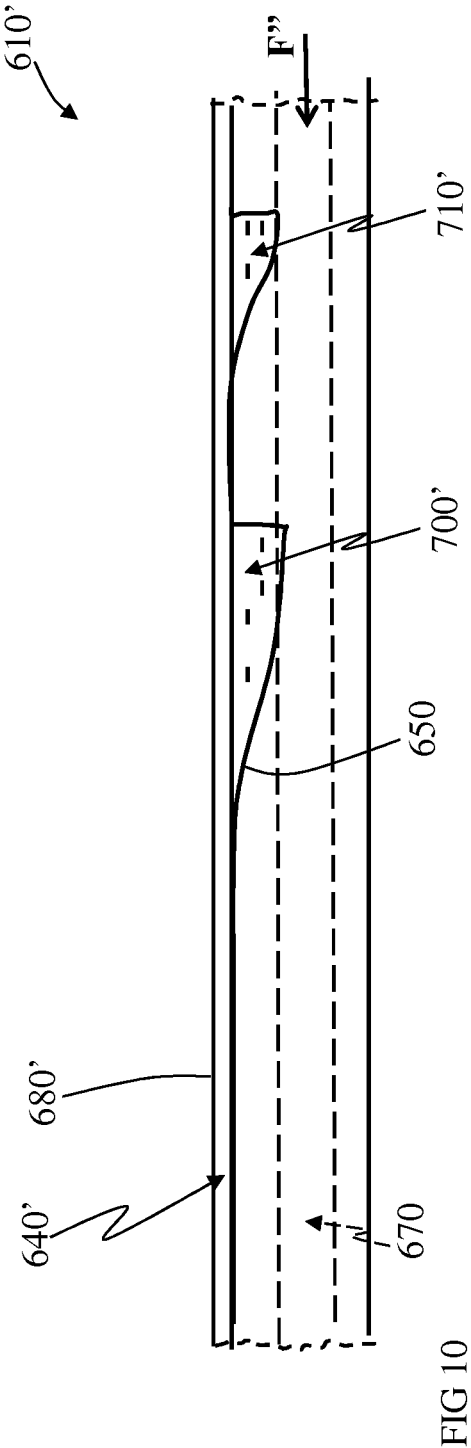
FIG 9
FIG 10

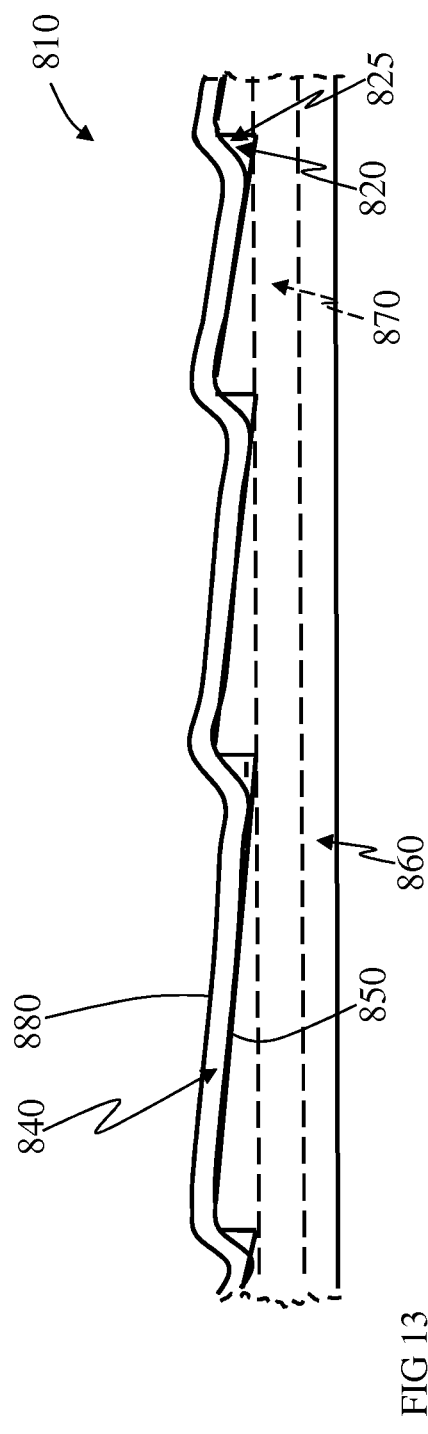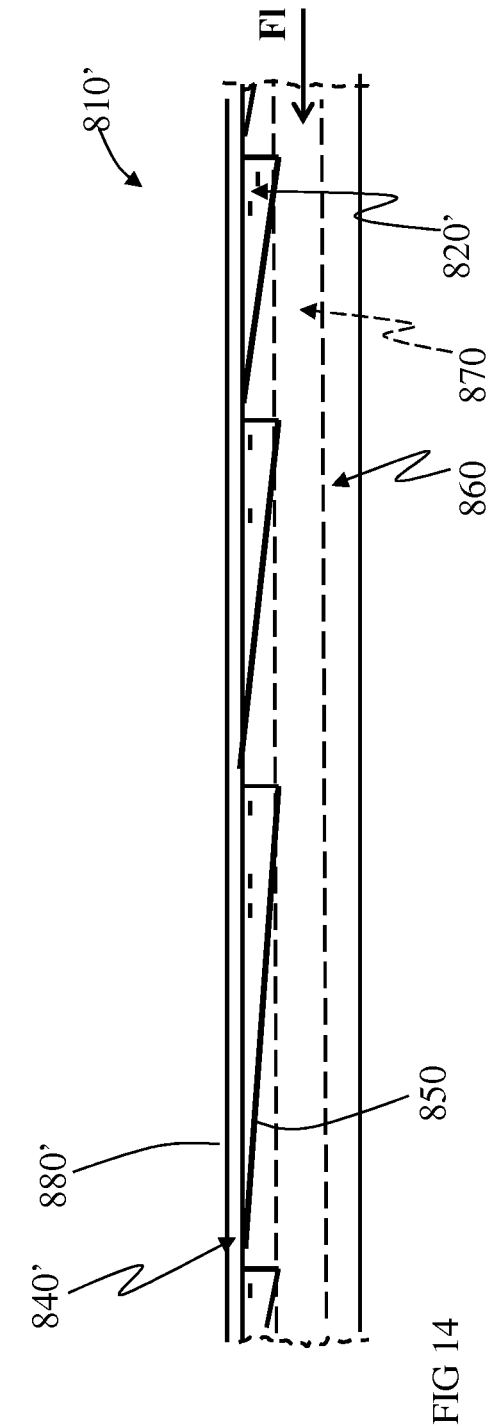
FIG 13
FIG 14

REMOTE MULTIFOCAL TO MONOFOCAL OPTIC CONVERSION

The present application claims priority from U.S. Provisional Patent Application Ser. No. 61/711,092 filed Oct. 8, 2012. This applications is to be incorporated in its entirety into the present application with this reference.

DESCRIPTION

Field of the Invention

The present invention relates generally to a switchable lens that changes image quality at a focus position upon remotely affecting the optical surface of the lens. More particularly, the present invention relates to an ophthalmic multifocal switchable lens that changes image quality of each far and near images by remotely affecting the multifocal surface shape of the lens.

Background of the Invention

Ophthalmic implants in the present invention is defined as a multifocal switchable lens suitable for placement inside the eye such as aphakic and phakic intraocular lenses or implants placed in posterior or anterior eye chamber and also included are artificial corneas and corneal implants or inlay. For detailed explanation of the lens of the present invention, the ophthalmic application for presbyopia correction by intraocular lens is used.

There is a significant effort to develop a lens for presbyopia correction in a form of multifocal refraction or diffractive multifocal lenses that produce multiple foci for far and near vision. Though a multifocal optic has achieved certain success in its application to intraocular lenses, their major drawback is a reduced image quality due to multiple foci. A reduced image quality is manifested in a form of image contrast reduction and halo/glare around the image. This limitation places a significant burden on surgeons in terms of a patient selection for a multifocal implant and more involved post-operative follow up as some patients complain on their vision quality with a multifocal optic. A small percentage of patients can't even tolerate the vision quality produced by multifocal implants and require a lens exchange for monofocal implants. A lens exchange is fundamentally invasive and a highly undesirable procedure that caries possible complications. The issue is that surgeons can't predict which patient would require a lens exchange despite a stringent patient selection thus leading to a limited use of a multifocal optic in their practice.

It has been practiced to control a multifocal optic deficiency by shifting a larger fraction of light to far focus because far vision is where the vast majority of the visual issues have been reported and shifting more light for far vision reduces a contribution of near image onto far image quality. However, this helps only to some degree. Portney in the U.S. Pat. No. 8,287,593 entitled, "ADJUSTABLE MULTIFOCAL INTRAOCULAR LENS SYSTEM" described a secondary enhanced lens implantation to control light split of previously implanted multifocal lens. (U.S. Pat. No. 8,287,593 is incorporated in its entirety with this reference.) The limitation of this option is that the adjustment still involves an invasive procedure. Sandstedt in the U.S. Pat. No. 7,988,285 entitled, "LIGHT ADJUSTABLE MULTIFOCAL LENSES" disclosed the use of optically reactive material for light adjustment to convert lens from a single focus to multifocal optic. Though highly challenging and likely impractical, conceptually it might be possible to have a reverse procedure to convert from a certain type of multifocal design to a monofocal one though it has not been described for light adjustable material. Sacharoff in the U.S. Pat. No. 8,231,673 entitled, "NON-INVASIVE POWER ADJUSTABLE INTRAOCULAR LENS" disclosed a microstructure within the IOL that places the intraocular optic under tension. The microstructure is operable to be broken in a controlled manner to release tension in the intraocular optic and reshape it for a power change as a whole. The cited reference was included here to avoid confusion between a lens power adjustment as a whole versus an adjustment of a light split between far and near vision which is the subject of the present application.

Optical switchable technology has been disclosed by Portney in U.S. patent application Ser. No. 13/247,840 for "SUB-ELEMENTS BASED SWITCHABLE CELL" and U.S. patent application Ser. No. 13/626,118 for "ELASTIC FILM BASED SWITCHABLE CELL," both of which are incorporated in full with these references.

A lens in accordance with the U.S. patent application Ser. No. 13/626,118 includes a switchable cell consisting of optical substrate with diffraction surface called guiding surface, elastic film in contact with the diffraction guiding surface, optical fluid called a matching fluid that fills a space between the film and guiding surface called transparent chamber and a channel to transfer the matching fluid in and out of the transparent chamber. The operation of the switchable optic in accordance with the U.S. patent application Ser. No. 13/626,118 relies on the ability of matching fluid to optically mask the guiding surface resulting in light interaction with a matching fluid surface instead of the guiding surface. A shape of the matching fluid surface is controlled by the film shape and by changing a shape of the film one can control a shape of the matching fluid surface thus controlling an image position of the corresponding refractive-diffractive lens.

A switchable cell according to the U.S. patent application Ser. No. 13/626,118 changes light flux between refraction focus in the relaxed state when the matching fluid is transposed to the transparent chamber and diffraction focus in the active state when the matching fluid is transposed from the transparent chamber for the film to conform to the guiding surface shape. The term "relaxed" state referenced to a film condition where a strain of the film is close to a minimum vs. the film in "active" state where the film at large takes a shape of the guiding surface thus manifesting an elevated strain. The corresponding optical states of the switchable cell are also called relaxed and active states. The disclosed technology in the U.S. patent application Ser. No. 13/626,118 was applied to the accommodating optic and the disclosure of aphakic accommodating lens application (FIGS. 4 through 9) to be incorporated in its entirety into the present application.

For reference, a focusing ability of a refraction surface depends on a surface curvature and diffraction surface focusing ability depends on a diffraction surface periodic structure defined by the widths of the diffraction grooves. In terms of a multifocal surface, a ratio of light split between far and near foci by a refraction multifocal surface is determined by a ratio of multifocal surface areas allocated to far and near vision and by a diffractive multifocal surface by a diffraction groove height. The corresponding explanations can be found in Portney's U.S. Pat. No. 5,225,858 entitled, "MULTIFOCAL OPHTHALMIC LENS" in regard to refraction multifocal optic and Portney's U.S. Pat. No. 7,073,906 entitled, "ASPHERICAL DIFFRACTICE OPH- THALMIC LENS" in regard to diffractive multifocal optic, both of which are incorporated in full with these references.

SUMMARY OF THE INVENTION

A multifocal switchable lens according to the present invention incorporates a switchable cell and optical surfaces. A multifocal switchable lens according to the present invention is a lens with the structure that allows controlling the image quality at distance and near foci or fields by remotely shifting a larger fraction of light allocated to one of the foci with the corresponding reduction of a fraction of light allocated to the other focus. An optical surface can be a part of a switchable cell or part of a separate optical element that together with switchable cell form multifocal switchable lens.

A switchable cell of the present invention is an opto-mechanical device that utilizes mechanical optical control of a ratio of light split between far and near foci of a multifocal switchable lens with the help of so called formable surface of a multifocal shape of a deformable element. Deformable element may be an elastic film or sub-elements mutually connected by thin members. A deformable element manifests elevated strain condition called active state to create formable surface of a multifocal shape. The strain of a deformable element is controlled by a chamber, so called transparent chamber, adjacent to the deformable element at the opposite side from the formable surface and filled with an optical fluid called a matching fluid. A refractive index of a matching fluid matches or is very close to the refractive index of deformable element material or another element material which is in contact with the deformable element. The amount of matching fluid in the transparent chamber is reduced to elevate a strain condition of the deformable element for an active state and this elevated strain condition is maintained by preventing a matching fluid flow into the transparent chamber to reduce the deformable element strain.

Besides a switchable cell, a multifocal switchable lens also contains a channel to enable a matching fluid transfer into a transparent chamber of the switchable cell, and a means to prevent a matching fluid flow into transparent chamber. A multifocal switchable lens also contains a holding chamber with expanded volume to include a balance of matching fluid required to increase the transparent chamber volume for reducing the strain of the deformable element close to its minimum level, to its so called relaxed state, if the balance of matching fluid is allowed to flow from the holding chamber to the transparent chamber with a removal of the means controlling the flow. In the relaxed state the formable surface of the deformable element or its part becomes a monofocal refractive surface usually for far vision.

In practice, a multifocal switchable lens is implanted in the eye. No image quality adjustment is required if a patient accepts a multifocal vision provided by the multifocal switchable lens. A switchable characteristic of a multifocal switchable lens comes into play only if a patient is substantially unhappy about the vision outcome. If required, a flow of a matching fluid from a holding chamber to the transparent chamber is allowed. It is performed by affecting the means that prevents a matching fluid flow. This in turn reduces or eliminating a light flow for near vision thus improving far vision quality without an invasive procedure involving an opening the eye. The process is called a switching process. Note that "near" vision in the present invention is used in a general term corresponding to a light not allocated to far vision and may include intermediate vision.

Two embodiments of the present invention are disclosed in the present application and include an elastic film based switchable cell and a sub-elements based switchable cell for a multifocal switchable lens. An elastic film based switchable cell has been disclosed in the present application for a diffractive multifocal switchable lens and refraction multifocal switchable optic.

A switchable cell in accordance with the present invention consists of at least three elements: (1) an optical substrate with a multifocal guiding surface on it, (2) an elastic film (deformable element) that at large takes a shape of the multifocal guiding surface, and (3) a chamber between elastic film and multifocal guiding surface of the optical substrate filled with optical fluid of refractive index which is equal to or up to about 0.03 unit different from the refractive index of the optical substrate material. The chamber is called the "transparent chamber" and the optical fluid is called "matching fluid" because desirably, its refractive index matches the refractive index of the optical substrate material at least at one of wavelengths. The matching is important in the visual spectrum defining switchable cell operation wavelengths and desirable in green color part of the spectrum in an ophthalmic application. A multifocal guiding surface of a switchable cell may be a refraction multifocal surface or diffractive multifocal surface or a combination of refraction and diffractive multifocal zones. These three element combinations form the "3-element switchable cell". The film is free-standing or bonded to the guiding surface of the optical substrate.

A switchable cell may also consists of five elements: (1) an elastic film, (2) an optical substrate with multifocal guiding surface, (3) a transparent chamber between the elastic film (deformable element) and optical substrate multifocal guiding surface filled with matching fluid, (4) an optical membrane situated next to the elastic film at the opposite side from the optical substrate and (5) a chamber between the elastic film and optical membrane filled with optical fluid of a refractive index that is differ from the refractive index of the optical substrate material at the operational wavelengths, this is the so called "non-matching fluid". The corresponding chamber is called the "active chamber". A switchable cell consisting of five elements described above is called the "5-element switchable cell". Thus, the 5-element switchable cell is comprised of the 3-element switchable cell plus the optical membrane forming active chamber filled with non-matching fluid. A non-matching medium is either ambient medium in case of 3-element switchable cell or a medium of the active chamber in case of 5-element switchable cell. The non-matching medium adjacent to the film at the opposite side from the transparent chamber can be aqueous humour, gas, stroma, tear layer, etc., depending on the application of the switchable lens of the present invention.

The external surface of the film facing the non-matching fluid is called the "formable surface". Because a shape of the matching fluid is formed by the film and equivalent to the formable surface shape of the film or can be adjusted by a thickness variation along the film, the formable surface describes optical states of a switchable cell instead of referencing to a matching fluid surface shaped by the film.

A transparent chamber can be a set of transparent chambers each formed within an individual groove of a multifocal diffractive guiding surface or individual zone of a multifocal refraction multizonal guiding surface. A set of transparent chambers is created by bonding the film at each diffractive groove or refraction zone. A set of transparent chambers as a whole is connected to a holding chamber by a channel or each transparent chamber of the set is connected to a holding chamber by an individual channel with a mean at each individual channel to prevent a matching fluid flow from the holding chamber to the transparent chamber. A switchable cell with individually allowed matching fluid flow to each transparent chamber of a set is called a "tunable switchable cell".

A multifocal switchable lens according to the present invention is implanted with its switchable cell being in the active state to provide a multifocal performance controlled by the multifocal guiding surface. A holding chamber is expanded to include a balance of matching fluid required for bringing the film into its "relaxed state" if the matching fluid is allowed to flow from the holding chamber to the connected to it transparent chamber. A strain elevation of the film in its active state together with a strain elevation of the holding chamber elastic wall create a force to push a balance of matching fluid from the holding chamber to the transparent chamber. This in turn reduces the film strain and brings the film into a relaxed state. In general, a balance of matching fluid in the holding chamber can vary to control a final shape of the film. Note, a film can be stretched out radially for an additional strain and a relaxed state of a portion of an elastic film within a transparent chamber is defined as a condition when the strain is close to a minimum magnitude for a type of film attachment in a switchable cell, i.e. a relaxed state of the film associates with a minimum potential energy.

In order to maintain a film in the active state a matching fluid flow between the holding chamber to the connected transparent chamber is prevented by a means. For instance, the connecting channel is blocked by a plastic membrane (blocking membrane) which can be locally melted by a focused laser beam for the channel opening for the matching fluid to flow from the holding chamber to transparent chamber. A readily available in ophthalmic practice is the Nd:YAG laser used for a posterior capsulotomy procedure which can be employed for opening a blocking membrane made of non-transparent material that absorbs the corresponding laser radiation, or a different type of laser can be used to remotely open the connecting channel between an holding chamber and transparent chamber. Different options are also available for a means to maintain a holding chamber in its expanded state. For instance, having a holding chamber bonded to two separate elements that are forcefully kept apart by another chamber (control chamber) for the holding chamber to maintain its expanded condition to hold a balance of matching fluid. This control chamber is another type of a means preventing a matching fluid flow to a connected to the holding chamber transparent chamber. The control chamber can be remotely pierced by a laser beam thus releasing the holding chamber and allowing a balance of matching fluid to flow to the connected transparent chamber of the switchable cell.

A multifocal switchable lens per the present invention allows (1) to convert multifocal lens into monofocal lens or tune the image quality if tunable switchable cell is involved, and (2) to conduct a conversion or tuning by a remote non-invasive switching procedure. With a switching procedure, a film as a whole or a portion of it is transformed into a relaxed state to refract light for far vision. It reduces a fraction of light allocated to near vision in tuning or totally eliminating light flux for near vision in conversion to a monofocal optic. A tuning allows a preservation of some level of near vision if the resulted multifocal vision turns out to become acceptable for a patient. If the vision quality is still unacceptable, another tuning step is undertaken until a total removal of multifocality by this virtual "lens exchange" from a multifocal optic to monofocal optic.

With virtual "lens exchange" the resulted monofocal lens can also become an accommodating multifocal switchable lens. A construction of accommodating switchable lens for aphakia has been disclosed in the U.S. patent application Ser. No. 13/626,118 (FIGS. 4 through 9) where the guiding surface was a monofocal diffractive surface. A monofocal diffractive guiding surface is replaced with a multifocal guiding surface and the film is maintained by a mean in the active state in accordance with the present invention. The accommodating ability comes into play if a communication between holding chamber and transparent chamber of the switchable cell is allowed and the holding chamber becomes an actuation chamber described in the U.S. patent application Ser. No. 13/626,118. In the resulting accommodating multifocal switchable lens, the accommodation occurs between a monofocal state for far vision when the film is in a relaxed state and multifocal state for near vision corresponding to the multifocal guiding surface when the film is in the active state. This is the reason the lens to be called accommodating multifocal switchable lens. According to a numerous clinical studies on multifocal intraocular lenses, a multifocality at near vision highly rarely presents at issue thus justifying the benefit of accommodating multifocal switchable lens.

A different switchable cell construction with deformable element consisting of sub-elements was disclosed in the U.S. application Ser. No. 13/247,840 for an accommodating optic. The switchable cell comprises an optical substrate also called a deformable element of the switchable cell. The optical substrate comprises annular shaped sub-elements connected to each other by thin members. There is also a transparent chamber formed by the deformable element/optical substrate and filled by a matching fluid. A refractive index of the matching fluid is equal to or up to about 0.03 unit different from the refractive index of the optical substrate material. All sub-elements are connected by thin deformable member together forming deformable element of the sub-elements based switchable cell. The sub-elements based switchable cell per the present invention creates a multifocal diffractive surface with the deformable members of the deformable element being deformed in an active state with the matching fluid is significantly removed from the transparent chamber and forcing bending of the sub-elements with corresponding elevation if deformable element strain. The surface of the deformable element opposite of the transparent chamber forms a multifocal diffractive surface in active state and is called a formable surface. As a result, a multifocal switchable lens is formed to provide a multifocal performance for far and near vision for the corresponding multifocal switchable lens. A multifocal switchable lens contains a sub-elements based switchable cell, optical surfaces, a holding chamber to maintain a balance of matching fluid, a channel connecting the holding and transparent chambers and a means to prevent a balance of matching fluid to flow from the holding to transparent chamber. A means to keep sub-elements based switchable cell in an active state is equivalent to a means used in an elastic film based switchable cell and described in present application.

Upon a removal of the means for holding the optical substrate as a deformable element in the active state, a balance of matching fluid flows into the transparent chamber and the optical substrate takes a relaxed state with its sub-elements formable surface becoming a monofocal refraction surface for far vision. This is the so called switching process. The switching process allows a virtual "lens exchange" from a multifocal optic to a monofocal optic with the use of the sub-elements based switchable cell.

The technology allows one time back reversal from the monofocal optic resulted from the conversion of the active state of the switchable cell to its relaxed state back to the original multifocal optic defined by the multifocal guiding surface. This is accomplished by piercing/rupturing/breaking/removing the elastic film of the switchable cell by a laser or other means to then allow the matching fluid between the film and guiding surface to diffuse into outside medium in a 3-element switchable cell. As a result, the matching fluid is replaced by the ambient fluid acting as the non-matching fluid and the multifocal performance is restored. A need for such back reversal may arise if the patient become disappointed in losing near vision and would like to go back to the original multifocal performance despite a possible optical effect such as halo and glare they experienced earlier with switchable multifocal IOL implantation.

The technology also allows a conversion of the implanted switchable lens with switchable cell in relaxed state in a monofocal performance for a potential future conversion to the multifocal state provided by the switchable cell multifocal guiding surface via piercing the elastic film adjacent to the multifocal guiding surface and letting matching fluid diffuse out to the external medium thus replacing the matching fluid with a non-matching fluid. The resulted switchable lens is converted from a monofocal lens to a multifocal lens Other features and advantages of the present invention will become apparent from the following more detailed description, when taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 shows a simplest form of switchable cell configuration as a circular disc with rectangular cross-section and multifocal diffractive guiding surface.

FIG. 2 demonstrates a segment of cross-section of preferred embodiment of elastic film based switchable cell in an active state where the matching fluid is largely removed from the transparent chamber where the switchable cell of this embodiment includes two chambers filled with optical fluids, separated by the elastic film where the film at large takes a shape of a diffractive multifocal guiding surface of the optical substrate in order to manifest a multifocal performance by the corresponding multifocal switchable lens.

FIG. 3 demonstrates the same section of the switchable cell cross-section shown on FIG. 2, but the switchable cell is in a relaxed state where a balance of matching fluid is released into the transparent chamber to mask the multifocal diffractive guiding surface in order to produce single focus performance.

FIG. 5A demonstrates a front view of a multifocal switchable intraocular lens in an active state with the channel connecting a holding chamber and transparent chamber being blocked where the configuration disclosed is applied to a multifocal switchable lens with a non-tunable switchable cell for a virtual "lens exchange" from a multifocal switchable intraocular lens onto monofocal refraction intraocular lens where similar tunable or non-tunable switchable cell configuration can be applied to any implantable ophthalmic lens.

FIG. 5B demonstrates a side view of the multifocal switchable intraocular lens per FIG. 5A where the lens optic is plano-convex shape with flat posterior optical surface where 3-element switchable cell in active state is located where the formable surface of multifocal diffractive shape of the switchable cell forms posterior optical surface of the multifocal switchable lens.

FIG. 7 demonstrates a segment of switchable cell cross-section analogous to one shown on the FIG. 2 but describing a preferred embodiment of a tunable switchable cell where the matching fluid is largely removed from the transparent chambers for the film at large takes a shape of the multifocal guiding surface where each individual transparent chamber is formed within a single diffractive groove or a small number of grooves by bonding the film at the groove ridges.

FIG. 8 demonstrates the same section of the switchable cell cross-section shown on FIG. 7 with the tunable switchable cell being in a relaxed state at one portion of the film where a balance of matching fluid is allowed to flow to the transparent chamber within this portion of film where, as a result, the matching fluid masks the multifocal diffractive guiding surface within the transparent chamber of the diffraction groove where this allocates a light passing though the area of the film over this groove to far vision and this in turn shifts a larger portion of light to far vision in a step corresponding to the area of the relaxed film portion.

FIG. 9 demonstrates a segment of a switchable cell cross-section as a preferred embodiment of a switchable cell in the active state where the matching fluid is largely removed from a transparent chamber and a multifocal guiding surface is a multifocal refraction surface where the film at large takes the shape of the multifocal refraction guiding surface of a corresponding multifocal switchable lens and where a switchable cell may include one pair of far and near zones or more than 2 pairs of zones.

FIG. 10 demonstrates the same section of the switchable cell cross-section shown on FIG. 9 with a switchable cell being in a relaxed state to transform the film within both transparent chambers over the near zones to the relaxed state where the matching fluid masks the near zones of the multifocal guiding surface to allocate a light passing though these zones to far vision where it is also possible to incorporate a tunable switchable cell with multifocal refraction multizonal guiding surface by switching only a portion of the film allocated to a near zone into relaxed state.

FIG. 13 demonstrates a segment of cross-section of preferred simplest embodiment of elastic film based switchable cell in an active state where the matching fluid is largely removed from the transparent chamber where the switchable cell of this embodiment includes a chamber filled with optical fluid between the elastic film and diffractive multifocal guiding surface of the optical substrate in order to manifest a multifocal performance by the corresponding multifocal switchable lens.

FIG. 14 demonstrates the same section of the switchable cell cross-section shown on FIG. 13, but the switchable cell is in a relaxed state where a balance of matching fluid is released into the transparent chamber to mask the multifocal diffractive guiding surface in order to produce single focus performance.

DETAILED DESCRIPTION OF THE PREFERRED EMBODIMENTS

Figure 6:
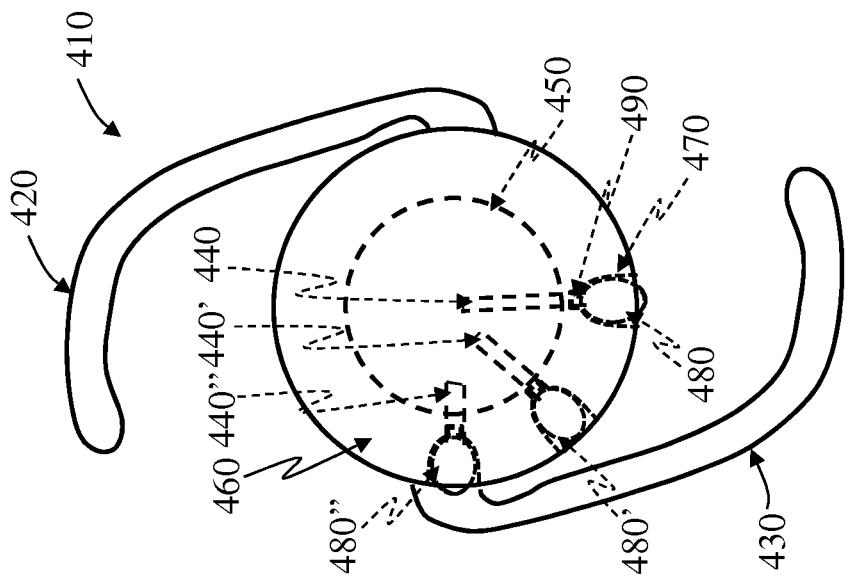
FIG. 6 demonstrates a front view of a multifocal switchable intraocular lens in active state with blocked channels connecting a set of holding chambers and set of transparent chambers where the configuration is applied to a multifocal switchable IOL with a tunable switchable cell for tuning the multifocal image quality in steps by incrementally increasing a fraction of light allocated to far vision where similar tunable switchable cell configurations can be applied to any implantable ophthalmic lens.

FIG. 1 shows a simplest form of switchable cell as a circular disc of D≈3-8 mm diameter and rectangular cross-section of W≈0.05-0.4 mm thickness in ophthalmic applications. The optical axis 100 and segment 110 of the switchable cell are shown.

FIG. 2 demonstrates the segment 110 of the cross-section of a preferred embodiment of a switchable cell in the active state. The switchable cell of this embodiment includes transparent chamber 120 filled with matching fluid 125 and active chamber 130 filled with non-matching fluid 135, separated by the film 140. The active chamber 130 is situated between film 140 and membrane 190. The film 140 is free-standing or bonded to the ridges of multifocal guiding surface 150 produced on the optical substrate 160. Guiding surface 150 is shown as blazed diffraction surface of period L as one of the periods within the segment 110. The channel 170 is shown to penetrate the deepest portions of the grooves of the guiding surface 150.

The optical substrate or optical membrane each may include flat or curved optical surface either at front or back surface or both surfaces. A curved surface within a switchable cell provides a refraction power to the switchable cell.

Film 140 can be made of different elastics, for instance with polydimethylsiloxane, also known as PDMS. The PDMS is a Si based organic polymer that has found wide applications in MEMS and microfluidic device fabrication, soft lithography, contact lens manufacturing and device encapsulation. The PDMS material is easily available as SYLGARD 184 Silicone Elastomer Kit from Dow Corning, with mixing in a 1:10 weight ratio. It is inexpensive and the fabrication processes for thin film with PDMS includes spin-casting, soft lithography or molding.

The optical substrate 160 can be made of any appropriate optical material used in ophthalmic application inside the eye which maintains guiding surface shape with the film compression in the active state, i.e. not too soft material. For instance, in IOL application, it can be silicone material (refractive index 1.41 and higher) or hydrophobic acrylic (refractive index 1.46 to 1.56) or even PMMA. Optical fluids of wide range of refractive indices to serve as matching fluid are available. For instance, Laser Liquid from Cargille Laboratories offers optical fluids between 1.293-1.578 refractive indices that are colorless, stable, biocompatible and inert.

The surface facing the active chamber 130 is formable surface 180 which is used to demonstrate optical switching to a relaxed state of the film/switchable cell. The formable surface 180 takes blazed diffractive surface shape of period L at the location of the segment 110 and groove height H' which is practically equivalent to the height H of the guiding surface 150 (within minute compression of the film at the groove ridges). It becomes a multifocal diffraction surface of the same periodicity and height as the guiding surface 150.

The elastic film 140 must maintain continuity and, as a result, it has a deviation from the guiding surface in the areas 200 close to the step transitions 210 between the diffractive grooves, so called smoothing area.

Technically, conformance of film 140 to the guiding surface 150 is defined as L'/L where L is a selected period of the guiding surface and L' is the width of the film conforming to the shape the guiding surface at the period L. A non-conformed width S of a given groove L is S=L−L' and defines a smoothing area or S-dimension. A multifocal guiding surface may also include its own "smoothing" instead of a step transition between the grooves. A conformance around 70% or higher is expected at the smallest period in the film's active state of a switchable cell with diffractive multifocal guiding surface per the present invention. The corresponding conformance values correspond to a reference "at large" used throughout the present application when discussing that elastic film "at large" takes a shape of the multifocal guiding surface. Further discussion of guiding surface periods, film thickness (3-10 µm), film FEA (Finite Element Analysis) and film conformance to the guiding blazed surface can be found in the U.S. patent application Ser. No. 13/626,118 and the corresponding disclosure to be incorporated in its entirety into the present application. Due to independence of the film strain to ocular elements involved in eye accommodation in the present invention, the film thickness can be 2-3 times thicker in the present invention than a thickness discussed in application Ser. No. 13/626,118.

Only a small fraction of total light passes through the formable surface within the smoothing area because the corresponding area occupies only a small fraction of optical surface. In addition, this small fraction of light is spread out outside an image itself because of a significant curvature of the surface within the smoothing area. Therefore, it is most likely that an intensity of the highly spread out light at each far and near images is fairly low and, as a result, its impact on an image quality of the multifocal switchable lens with the film being in active state is largely insignificant. Another difference between the disclosure in the present invention and the one in the '118 application is the guiding surface height. For instance, in example A of the FIG. 3 of the '118 application where the optical substrate was made of PDMS, the groove height was $H_{-1}$=8.4 µm for Kinoform performance. If the same substrate material is used in the present invention, the groove height is reduced in order to split the passing through the switchable cell light between different orders for a multifocal performance. For instance, for an equal split of light between zero order allocated to far vision and $-1^{st}$ order allocated to near focus, the height $H=H_{-1}/2=4.2$ μm. Use of materials with different refractive indices for the optical substrate with the same periodic structure of the guiding surface does not impact Add power between far and near foci and only impacts a groove height H that controls a light split between far and near vision.

FIG. 3 demonstrates the same section 110' of the cross-section of the switchable cell, shown in FIG. 2, but in a relaxed state. Substrate 160 with the guiding surface 150 on it and membrane 190 do not change in the switchable cell in a relaxed state. The film 140', transparent chamber 120' and active chamber 130' take different shapes due to a balanced amount of matching fluid has flown F from a holding chamber through the channel 170 to the transparent chamber 120' to bring the film 140' into a relaxed state. The formable surface 180' becomes a refraction surface of single focus as the matching fluid masks the multifocal guiding surface 150 and neutralizes multifocal performance of the multifocal switchable lens.

In a simpler form, the channel 170 can be made in a form of a trench channel, i.e. a channel cut across the cross-sections of the grooves of the guiding surface 150. Optical effect of the Trench channel in active state is likely negligible with narrow enough channel, say 100 microns or less. A trench channel can be made during a guiding grooves fabrication thus lowering cost of the production and desirably but not necessarily, made in a radial orientation to minimize a tearing of the film in transitions from active to relaxed state when the film strain is reduced. It also desirable to round trench channel edges for the same purpose.

In a 5-element switchable cell a volume of the optical fluid in the active chamber stays the same in active or relaxed states. This is accomplished by incorporating a flexible membrane in a side of the active chamber containing non-matching optical fluid. In a 3-element switchable cell, an ambient fluid acts as non-matching fluid adjacent to a formable surface of a switchable cell.

Figure 4:
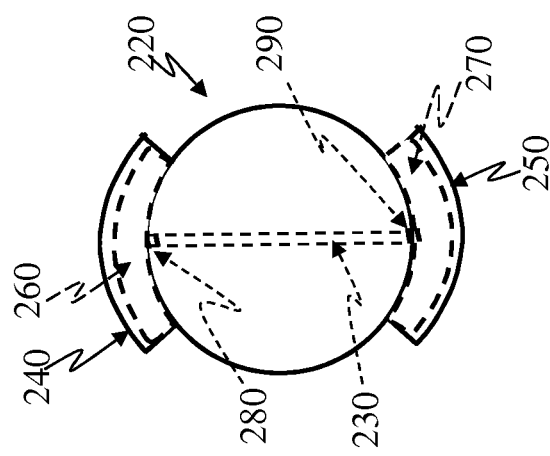
FIG. 4 illustrates a front view of a switchable cell of an accommodating multifocal switchable intraocular lens with internal actuation for aphakia where the overall lens construction is equivalent to one described in the FIG. 4 of application Ser. No. 13/626,118 for aphakic application with the differences are multifocal guiding surface, a holding chamber, a channel connecting the a holding chamber and transparent chamber and a mean preventing a balance of matching fluid to flow from holding to transparent chamber.

FIG. 4 illustrates a front view of switchable cell 220 of an aphakic multifocal switchable intraocular lens. The switchable cell 220 is connected to two external members 240, 250 that incorporate holding chambers 260, 270 correspondently. A holding chamber is formed by an elastic membrane to enable it to change its volume if the holding chamber is stretched out in the active state of the holding chambers to hold a balance of matching fluid required for a conversion the switchable cell into a relaxed state if the matching fluid is allowed to flow from the holding chamber to transparent chamber of the switchable cell.

The FIG. 4 includes two holding chambers but it is possible to have only one if the goal is only to convert the switchable cell from the active state to relaxed state. (It will be understood by one skilled in the art that multiple holding chambers may be used.) Two opposite holding chambers 260, 270 are likely beneficial if the goal is to convert an aphakic multifocal switchable lens into aphakic accommodating multifocal lens constructed similarly to one disclosed in the '118 application in FIGS. 4-9. The construction of the switchable cell 220 is equivalent to the construction of the switchable lens of the FIG. 4 of the '118 application except its guiding surface is multifocal diffractive surface and communication between the holding chambers 240, 250 with transparent chamber of the switchable cell is blocked by blocking membranes 280, 290.

The switchable cell 220 is converted from an active to relaxed state with opening the blocking membranes 280, 290 at the channel 230 for a balance of matching fluid to flow from the holding chambers 260, 270 to the transparent chamber of the switchable cell 220. The holding chambers then become actuation chambers of the resulted accommodating multifocal switchable intraocular lens with internal actuation.

The lens is called accommodating multifocal intraocular lens in the present invention because the accommodation occurs between a single focus intraocular lens for far vision with the switchable cell in relaxed state and multifocal intraocular lens for near vision with the switchable cell in the active state. Because the optical issues are largely occur for far vision, the resulted accommodating multifocal switchable lens still cures the multifocality issue of the original multifocal switchable lens with added benefit of accommodation between far and near vision. As another option, an accommodating multifocal lens as well as any switchable lens may also rely on external actuation by a Sensor Cell disclosed in the U.S. patent application Ser. No. 13/247,840.

External members 240, 250 are part of one optical member of the multifocal switchable lens and the holding chambers 260, 270 are bonded to this member at one side (front or back) with another side of the holding chambers are bonded to a separate optical member creating a construction similar to one disclosed in the '118 application at FIG. 7. The holding chamber is expanded to hold a balance of matching fluid thus keeping the optical members further apart. Instead of blocking membranes 280, 290, there is another option for a means for preventing a matching fluid flow from holding to transparent chamber. It is to include another chamber, so called control chamber, between the optical members to keep them further apart and, therefore, maintain the holding chambers in expanded condition. A switching process to convert switchable cell from active to relaxed state then involves piercing the control chamber to allow the holding chamber to release the flow of the balance of matching fluid to the transparent chamber for the lens to become accommodating multifocal switchable IOL.

A balance of matching fluid in holding chambers is created by pressing the film against the guiding surface by a surface similar to a mirror shape of the guiding surface shape thus squeezing the matching fluid out of the transparent chamber into connected to it holding chamber. A channel connecting holding and transparent chambers is then blocked by a blocking membrane to maintain the switchable cell in active state.

FIG. 5A demonstrates a front view of a multifocal switchable IOL 310 with optical body 360 and haptics 320, 330 to hold the IOL inside the eye. Its switchable cell 350 incorporates holding chamber 380 together with a switchable cell elements described above (film, substrate and so on).

In terms of the multifocal switchable lens 310 fabrication and operation. An annular groove which would become a holding chamber 380, is made in an optical substrate of the switchable cell outside the optical zone 370 within which the guiding surface is located. The annular groove is produced during guiding surface fabrication. The channel 340, trench channel for instance, connects a future transparent chamber 370 of the switchable cell 350 and the annular groove of a future holding chamber 380. The elastic film is then bonded to the substrate over the guiding surface to form transparent chamber and simultaneously over the annular groove to form a holding chamber 380 thus creating holding chamber and transparent chamber in one step. The chambers are filled with matching fluid and sealed with the condition to maintain film flatness. The film is pressed against the guiding surface by an exterior element facing the film surface shaped as a mirror shape of the guiding surface, i.e. the surfaces compliment to each other. The pressing the film by the external element squeezes the matching fluid from the transparent chamber into the holding chamber. The resulted active state of the film is maintained by injecting a plastic membrane 390 at the channel 340 in the intersection of the channel 340 and holding chamber 380 to block the matching fluid to flow back into transparent chamber after the pressure on the film by the external element is ceased. The plastic membrane 390 also divides the channel 340 creating a small portion 345 at the periphery from the holing chamber 380 which is slightly larger in volume the plastic membrane 390. A content of the portion 345 is expelled to create a significantly low pressure as compared with a pressure at the transparent chamber of the switchable cell 350. A switchable process of melting the plastic blocking membrane remotely by a laser beam and low pressure in the portion 345 sucks the melted blocking membrane material inside the portion 345 to open a communication between the holding chamber 380 and transparent chamber for a balance of matching fluid to flow to the transplant chamber and convert the switchable cell 350 from active to relaxed state. The switchable cell 350 is inserted into the lens body 360 to form a multifocal switchable lens. The same multifocal switchable lens assembly is applied to a lens for any ophthalmic multifocal application.

FIG. 5B demonstrates a side view of the multifocal switchable intraocular lens 310 per FIG. 5A. The lens includes haptics 320, 330. The lens optic is plano-convex shape with convex anterior optical surface 365 and flat posterior optical surface 375 where 3-element switchable cell 370 is situated. The formable multifocal diffractive surface 385 of the switchable cell 370 is the central part of the posterior optical surface 375 of the multifocal switchable lens 310. The holding chamber 380 is shown in circumference to the multifocal diffractive formable surface 385.

A switchable cell can also be imbedded into a multifocal switchable lens per the present invention to produce posterior optical surface of a curved shape. In this case a 5-element switchable cell with an optical surface is used or 3-element switchable cell is used with a space adjacent to its formable surface filled with a surrounding medium to act as non-matching fluid.

FIG. 6 demonstrates a front view of a multifocal switchable IOL 410 in active state where the channels 440, 440', 440" connecting the corresponding holding chamber 480, 480', 480" and transparent chambers of the switchable cell 450 are blocked. Holding chambers 480, 480', 480" are presented as small bubbles with elastic walls filled with matching fluid but also can be made by a similar arrangement descried in the FIG. 5A, 5B, i.e. a set of annular holding chambers connected to a set of transparent chambers. The switchable cell 450 consists of a set of transparent chambers formed by bonding the film to the multifocal guiding surface. In this case there is a set of 3 transparent chambers each connected to the corresponding 3 holding chambers 480, 480, 480". The transparent chambers are of annular shapes of different radii, one with small radius is connected to the holding chamber 480 by a longer channel 440, next of a larger annulus is connected to the holding chamber 480' by a shorter channel 440' and the largest annulus of the last transparent chamber is connected to the holding chamber 480" by the shortest channel 440".

Holding chamber 480 is bonded to the internal wall of the hollow chamber 470 placed at the periphery of the IOL optic body 460. As with a common IOL, the optic body 460 is held inside the eye by the haptics 420, 430. The holding chamber 480 includes a plastic blocking membrane 490 to prevent a flow of a balance of matching fluid from the holding chamber 480 to the transparent chamber of the switchable cell 450 through the channel 440. The holding chamber 480 is inserted through the external opening of the hollow chamber 470 and bonded at its internal side to the wall of hollow chamber 470. The bonding occurs upon a balance of matching fluid being squeezed from the corresponding transparent chamber of the switchable cell 450. The plastic blocking membrane 490 is then inserted to secure the corresponding transparent chamber in its active state. The same process is applied to other pairs of holding and transparent chambers.

FIG. 7 demonstrates a segment 510 of switchable cell cross-section analogous to one shown on the FIG. 2 but describing a preferred embodiment of a tunable switchable cell. The overall shape and structure are the same where the multifocal guiding surface 550 produced on the optical substrate 560 and the film 540 is bonded to the ridges 590, 600 and so on of the guiding surface diffraction grooves and the film 540 at large takes the shape of the guiding surface 550 with the matching fluid extracted from the spaces in between the film 540 and guiding surface 550 (active state). It results in formable surface 580 taking a multifocal diffractive surface shape that closely matches the multifocal diffractive surface shape of the guiding surface 550. The switchable cell splits light between far and near for a multifocal performance of the corresponding multifocal switchable lens. A matching fluid occupies spaces 520 and so on between the film 540 and guiding surface 550 thus forming multiple separate transparent chambers 520 and so on. In this case an individual transparent chamber is formed within a single diffraction groove by bonding the film at the groove ridges with the individual channel connecting each transparent chamber with the individual holding chamber.

Similar to the FIG. 2, the segment shown on FIG. 7 is part of 5-element switchable cell that includes a membrane 565 and active chamber 530 between the membrane 565 and film 540 filled with non-matching optical fluid.

The optical substrate 560 includes a set of channels individually connecting a set of transparent chambers with a set of holding chambers to with a mean in each channel to maintain active state of all film portions over transparent chambers. For instance, the channel 570 connecting the transparent chamber 520 affects only the active state of the film portion of width $L_j$ bonded to the ridges 590 and 600 of the guiding surface 540. The corresponding switchable cell is called tunable switchable cell.

FIG. 8 demonstrates the same section 510' of the tunable switchable cell cross-section shown on FIG. 7. If it is required, the means that prevents a flow of a balance of matching fluid from holding chamber is removed and a balance of matching fluid flows F' to the transparent chamber 520' through the channel 570 resulting in the film 540' taking a relaxed state only between the ridges 590, 600 of the guiding surface 550. The formable surface 580' becomes refraction surface for far vision between the ridges 590, 600. The rest of the film 540' is still in active state to split light for a multifocal performance but now a fraction of light passing through the annulus of width Lj is not involved in light split but becomes a refraction portion of the formable surface 580' to refract light for far vision. The described switchable cell tuning increases a fraction of light allocated to far vision and proportionally reduces a fraction of light allocated to near vision thus reducing impact of near image on far image quality.

The same switching process can then be applied to the tunable switchable cell for another incremental reduction in a fraction of light allocated to near vision. The process describes incremental vision quality tuning until a total virtual "lens exchange" occurs from a multifocal optic to a monofocal optic.

FIG. 9 demonstrates a segment 610 of a switchable cell cross-section and as a preferred embodiment of a switchable cell in the active state where the matching fluid is largely removed from the transparent chambers 700, 710 and so on situated between the film 640 and guiding surface 650 produced on the optical substrate 660. The multifocal guiding surface is a multifocal refraction surface. The film 640 is bonded to the edges 720, 730 of the multifocal refraction guiding surface or at a part or whole area of the multifocal refraction guiding surface 650 allocated for far vision. FIG. 9 demonstrates a 3-element switchable cell.

The cross-section of guiding surface 650 shows two far vision zones $Z_{jF}$, $Z_{(j+1)F}$ and two near vision zones $Z_{jN}$, $Z_{j+1)N}$. In a preferred embodiment the guiding surface within a far vision zone is largely flat and within a near zone is curved to provide a higher power for near vision. There are steps 620, 620' at the exterior edge of the near zones to bring the guiding surface shape back to keep the level of far vision zones all the same. The step height is H" is shown to be the same at both steps 620, 620' which might be the case for certain widths of near vision zones and is not always the case. A step height in a multifocal refraction guiding surface is usually in the order of several tens of microns which is substantially larger than in case of a multifocal diffractive guiding surface where a height is in microns.

A channel 670 is at the lowest part of a near vision zone to facilitate largest possible removal of the matching fluid for largest possible conformance of the film 640 and formable surface 680 to the multifocal guiding surface 650. Due to continuity of the film, there is a slight non-conformance widths $\delta_j$ and $\delta_{(j+1)}$. where transparent chambers 700, 710 are. A conformance around 70% or higher is expected within a near zone of a film's active state of a switchable cell with multifocal refraction guiding surface per the present invention. A non-conformance area is substantially smaller the area occupied by far and near zones and in addition, the formable surface is highly curved within a non-conformance area to spread light within a wide area at an image plane thus minimizing an effect of the non-conformance area on the image quality formed by the multifocal switchable lens.

FIG. 10 demonstrates the same section 610' of the switchable cell cross-section shown on FIG. 9 with a switchable cell being in a relaxed state with the film 640' within both transparent chambers 700', 710' being in relaxed state. If required due to a multifocal vision issue, a balance of matching fluid is allowed to flow F'" to the transparent chambers 700', 710' through the channel 670 to form the film 640' in relaxed state that masks near vision zones of the multifocal refraction guiding surface 650. The formable surface 680' takes the shape for far vision only though out the whole segment 610' of the switchable cell. The process is applied to the whole switchable cell for a virtual "lens exchange" from a multifocal optic to monofocal optic. Similar to the arrangement shown on the FIG. 7, 8, the switchable cell can be a tunable switchable cell with multifocal refraction guiding surface if a set of the transparent chambers corresponding to near zones is connected to a set of holding chambers by individual channels with a mean preventing a balance of matching fluid to flow from a holding chamber to connected to it transparent chamber.

Figure 11:
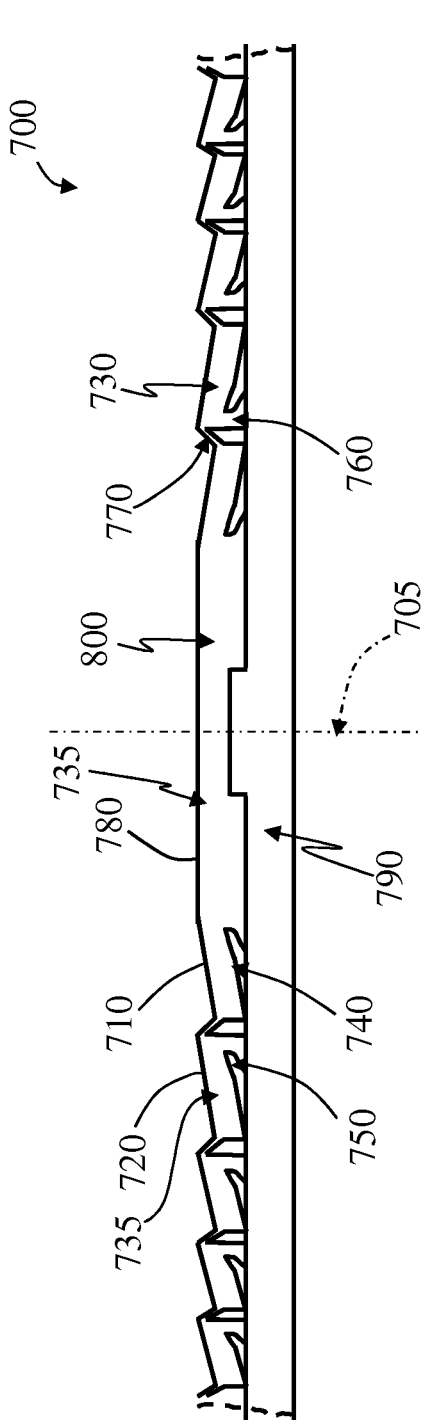
FIG. 11 demonstrates a segment of switchable cell cross-section where the switchable cell consists of sub-elements connected by thin members similar to an accommodating cell described in the U.S. application Ser. No. 13/247,840 where the optical substrate of the switchable cell consists of bent sub-elements to form formable multifocal diffractive surface for far and near vision with the switchable cell being in active state and the corresponding switchable cell is part of a multifocal switchable lens that includes the switchable cell, holding chamber, a channel connecting the holding and transparent chamber and a means to prevent a balance of matching fluid to flow from holding to transparent chamber.

FIG. 11 demonstrates cross-section of a section 700 of a switchable cell with overall dimensions similar to the one shown on FIG. 1. A composition of this switchable cell is similar to accommodating cell described in U.S. patent application Ser. No. 13/247,840. The section 700 of the switchable cell comprises an optical substrate 800 attached to the supporting substrate 790, both being optically transparent. The optical substrate 800 consists of sub-elements 730 and so on and central element 735. Each sub-element is of annular shape. All sub-elements are attached to the supporting substrate 790 at either internal or external side of a sub-element to allow bending the sub-elements towards the center or periphery of the switchable cell. For instance, sub-element 730 is attached internally to the supporting substrate 790 by the element 760. All sub-elements are also connected to each other by very thin member that substantially thinner a thickness of a sub-element itself. For instance, a thin deformable member 770 connects sub-element 730 with the adjacent sub-element at its internal side. There is a chamber represented by the connected spaces 740, 750 and so on between the optical substrate 800 and supporting substrate 790 filled with matching fluid with a refractive index matching the refractive index of a material of the optical substrate 800. All these spaces 740, 750 and so on are connected by a channel and together are called a transparent chamber of the disclosed sub-elements based switchable cell. All sub-elements are bent in the active state of the substrate by squeezing the matching fluid from the transparent chamber to produce diffractive grooves 710, 720 and so on together creating a multifocal diffractive surface for far and near vision. The connecting thin members 770 and so on are stretched and manifest an elevated strain characterizing an active state of the optical substrate 800 and corresponding switchable cell 700. The surface of the optical substrate 800 opposite from transparent chamber is called formable surface and is shaped as a surface relief, i.e. multifocal blazed diffractive surface. The active state of the optical substrate and the corresponding switchable cell is maintained by a means preventing a flow of a balance of matching fluid into the transparent chamber from a holding chamber. Structures of a means and holding chamber have been described in the disclosed above elastic film based switchable cells, FIG. 5A, for instance.

The central element 735 is sized to be equivalent to a diameter of the central groove of the corresponding formable multifocal diffractive surface and is maintained in non-active state with its surface being for far vision. The formable surface 780 is facing a non-matching fluid to manifest a multifocal diffractive performance. The disclosed switchable cell is a part of an ophthalmic multifocal switchable lens to provide far and near vision.

Figure 12:
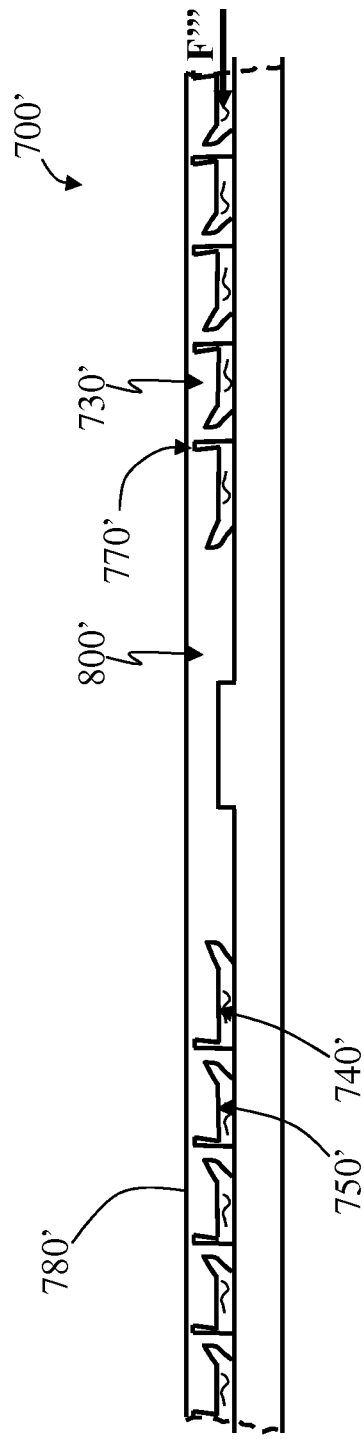
FIG. 12 demonstrates the same section of the switchable cell cross-section shown on FIG. 11 with the switchable cell being in a relaxed state where the sub-elements together with thin members connecting them form formable single focus refraction surface for far vision.

FIG. 12 demonstrates the same section 700' of the switchable cell described in FIG. 11 but in relaxed state where the means that maintains the switchable cell in the active state is removed and a balance of matching fluid flows F'" into the transparent chamber represented by 740', 750' and so on from a connected to it holding chamber. The substrate 800' is in a relaxed state with thin members 770' and so on together with the sub-elements 730' and so on taking a state close to its minimum strain, i.e. the substrate 800' is in relaxed state. The fordable surface 780' formed by the sub-elements 730' and so on becomes a single focus refractive surface for far vision thus demonstrating a virtual "lens exchange" from a multifocal diffractive optic to monofocal refraction optic.

FIG. 13 demonstrates the segment 810 of the cross-section of a preferred embodiment of a switchable cell in the active state. The switchable cell of this embodiment includes transparent chamber 820 filled with matching fluid 825. The film 840 is free-standing or bonded to the ridges of multifocal guiding surface 850 produced on the optical substrate 860. Guiding surface 850 is shown as blazed diffraction surface. The channel 870 is shown to penetrate the deepest portions of the grooves of the guiding surface 850. The formable surface 880' is multifocal diffractive surface with periodic structure equivalent to the periodic structure of the multifocal guiding surface 850.

FIG. 14 demonstrates the same section 810' of the cross-section of the switchable cell, shown in FIG. 13, but in a relaxed state. Substrate 860 with the guiding surface 850 on it do not change in the switchable cell in a relaxed state. The film 840' and transparent chamber 820' take different shapes due to a balanced amount of matching fluid has flown Fl from a holding chamber through the channel 870 to the transparent chamber 820' to bring the film 840' into a relaxed state. The formable surface 880' becomes a refraction surface of single focus as the matching fluid masks the multifocal guiding surface 850 and neutralizes multifocal performance of the multifocal switchable lens.

Although several embodiments have been described in detail for purposes of illustration, various modifications may be made to each without departing from the scope and spirit of the invention. Accordingly, the invention is not to be limited, except as by the appended claims.

What is claimed is:

1. An ophthalmic multifocal switchable lens suitable for implantation in the eye, comprising:
    an optical substrate comprising a multifocal guiding surface to provide far and near foci;
    a deformable film in contact with the multifocal guiding surface;
    a transparent chamber formed between the multifocal guiding surface and the deformable film;
    where the transparent chamber is filled with a matching fluid, where the matching fluid has a substantially similar index of refraction compared to the optical substrate;
    a holding chamber filled with the matching fluid;
    a channel connecting the holding chamber to the transparent chamber; and
    a blocking membrane disposed within a portion of the channel blocking fluidic communication between the holding chamber and the transparent chamber;
    wherein the deformable film in a first state conforms to the multifocal guiding surface forming a multifocal lens and wherein the deformable film in a second state is a refractive surface characterized by a curvature forming a monofocal lens that maintains the far focus.

2. The lens of claim 1, including a membrane disposed on an opposite side of the deformable film and an active chamber formed between the opposite side of the deformable film and the membrane, wherein the active chamber is filled with a non-matching fluid, where the non-matching fluid has a substantially different index of refraction compared to the optical substrate.

3. The lens of claim 1, wherein the holding chamber comprises an elastic membrane configured to create an elevated pressure in the holding chamber over the transparent chamber.

4. The lens of claim 1, wherein the deformable film is conformally biased against the multifocal guiding surface when the blocking membrane is intact.

5. The lens of claim 1, wherein the deformable film is configured to be the refractive surface when the blocking membrane is ruptured.

6. The lens of claim 1, wherein the multifocal guiding surface comprises a multifocal diffractive guiding surface characterized by periodic grooves.

7. The lens of claim 1, wherein the multifocal guiding surface comprises a multifocal refraction guiding surface of zones of different optical powers.

8. The lens of claim 1, wherein the multifocal guiding surface comprises a plurality of ridges and where the deformable film is bonded to the multifocal guiding surface at the plurality of ridges.

9. The lens of claim 8, wherein the bonding of the deformable film to the plurality of ridges forms a plurality of transparent chambers.

10. The lens of claim 1, wherein the holding chamber comprises at least a portion of an annularly shaped holding chamber.

11. The lens of claim 1, wherein the blocking membrane comprises a laser-breakable blocking membrane.

12. An ophthalmic multifocal diffractive switchable lens suitable for implantation in the eye, comprising:
    an optical substrate having a first side comprising a plurality of annular shaped grooves forming a multifocal diffractive surface providing far and near foci;
    an optically transparent structure attached to the first side of the optical substrate;
    at least one transparent chamber formed between the plurality of annular shaped grooves and the optically transparent structure;
    a matching fluid disposed within the at least one transparent chamber having a substantially similar index of refraction compared to the optical substrate;
    a holding chamber filled with the matching fluid;
    a channel connecting the holding chamber to the at least one transparent chamber; and
    a blocking membrane disposed within a portion of the channel blocking fluidic communication between the holding chamber and the at least one transparent chamber;
    wherein the optically transparent structure in a first state forms a multifocal diffractive lens and wherein the optically transparent structure in a second state forms a monofocal lens of the far focus.

13. The lens of claim 12, wherein the multifocal surface comprises a multifocal guiding surface and wherein the optically transparent structure comprises a deformable film, wherein a membrane is disposed on a second side of the deformable film, wherein an active chamber is formed between the second side of the deformable film and the membrane, wherein the active chamber is filled with a non-matching fluid where the non-matching fluid has a substantially different index of refraction compared to the optical substrate.

14. The lens of claim 12, wherein the plurality of annular shaped grooves forming a multifocal surface comprises a plurality of annular shaped sub-element grooves bendable towards a periphery or center of the switchable lens.

15. The lens of claim 12, wherein the blocking membrane comprises a laser-breakable blocking membrane.

16. An ophthalmic multifocal switchable lens suitable for implantation in the eye, comprising:
    an optical substrate comprising a multifocal guiding surface providing far and near foci;
    a deformable film in contact with the multifocal guiding surface;

a transparent chamber formed between the multifocal guiding surface and the deformable film;

where the transparent chamber is filled with a matching fluid, where the matching fluid has a substantially similar index of refraction compared to the optical substrate;

a holding chamber filled with the matching fluid;

a channel connecting the holding chamber to the transparent chamber; and a means for preventing fluidic communication between the holding chamber and the transparent chamber;

wherein the deformable film in a first state conforms to the multifocal guiding surface forming a multifocal lens and wherein the deformable film in a second state forms a monofocal lens that maintains the far focus.

17. An ophthalmic multifocal switchable lens suitable for implantation in the eye, comprising:

an optical substrate having a first side comprising a plurality of annular shaped grooves forming a multifocal surface providing far and near foci;

an optically transparent structure in contact with the first side of the optical substrate;

at least one transparent chamber formed between the plurality of annular shaped grooves and the optically transparent structure;

a matching fluid disposed within the at least one transparent chamber having a substantially similar index of refraction compared to the optical substrate;

a holding chamber filled with the matching fluid;

a channel connecting the holding chamber to the at least one transparent chamber; and a means for preventing fluidic communication between the holding chamber and the at least one transparent chamber;

wherein the optically transparent structure in a first state conforms to the plurality of annular shaped grooves forming a multifocal lens and wherein the optically transparent structure in a second state is a refractive surface forming a monofocal lens that maintains the far focus.

* * * * *